(12) United States Patent
Kim et al.

(10) Patent No.: US 7,147,627 B2
(45) Date of Patent: Dec. 12, 2006

(54) BOWEL MANAGEMENT SYSTEM

(75) Inventors: Jae H. Kim, Daegu (KR); John S. Minasi, Amelia Island, FL (US); James G. Schneider, Chesterfield, MO (US); Nick Martino, Fernandina Beach, FL (US); Peter M. von Dyck, Fernandina Beach, FL (US)

(73) Assignee: Hollister Incorporated, Libertyville, IL (US)

( * ) Notice: Subject to any disclaimer, the term of this patent is extended or adjusted under 35 U.S.C. 154(b) by 712 days.

(21) Appl. No.: 10/225,820

(22) Filed: Aug. 21, 2002

(65) Prior Publication Data

US 2004/0039348 A1   Feb. 26, 2004

(51) Int. Cl.
*A61M 1/00* (2006.01)
*A61M 25/00* (2006.01)

(52) U.S. Cl. .................... 604/327; 604/525

(58) Field of Classification Search ............ 604/19, 604/27, 28, 30, 34, 500, 514–517, 93.01, 604/96.01, 99.04, 104, 275, 276, 277, 278, 604/523, 525, 317, 323, 327, 328, 335
See application file for complete search history.

(56) References Cited

U.S. PATENT DOCUMENTS 4,637,814 A    1/1987   Leiboff 5,569,216 A  * 10/1996  Kim ........................... 604/277
5,766,209 A     6/1998  Devonec
6,719,709 B1 *  4/2004  Whalen et al. ............. 600/587

FOREIGN PATENT DOCUMENTS

DE    2447996    4/1976
EP    0274415    7/1988
FR    2660561   10/1991

* cited by examiner

*Primary Examiner*—Catherine S. Williams
(74) *Attorney, Agent, or Firm*—Marshall, Gerstein & Borun LLP

(57) ABSTRACT

A bowel management system includes a waste collection catheter having at least two distinct sections. The first section is patient proximal when disposed in the patient's rectum and has durometer hardness in the range of about 50A to about 90A. The second catheter section is connected to the first section and has durometer hardness in the range of about 5A to about 49A. A selectively collapsible, substantially spherical retention balloon is attached coaxially and exterior of the first catheter section such that the proximal-most end of the retention balloon is coincident to the proximal-most end of the first section of the waste collection catheter, the substantially spherical retention balloon having an inflated size so as to be sufficiently large enough to retain the patient proximal end of the catheter in the patient's rectum without being so large as to trigger a defecatory response in the patient.

44 Claims, 13 Drawing Sheets

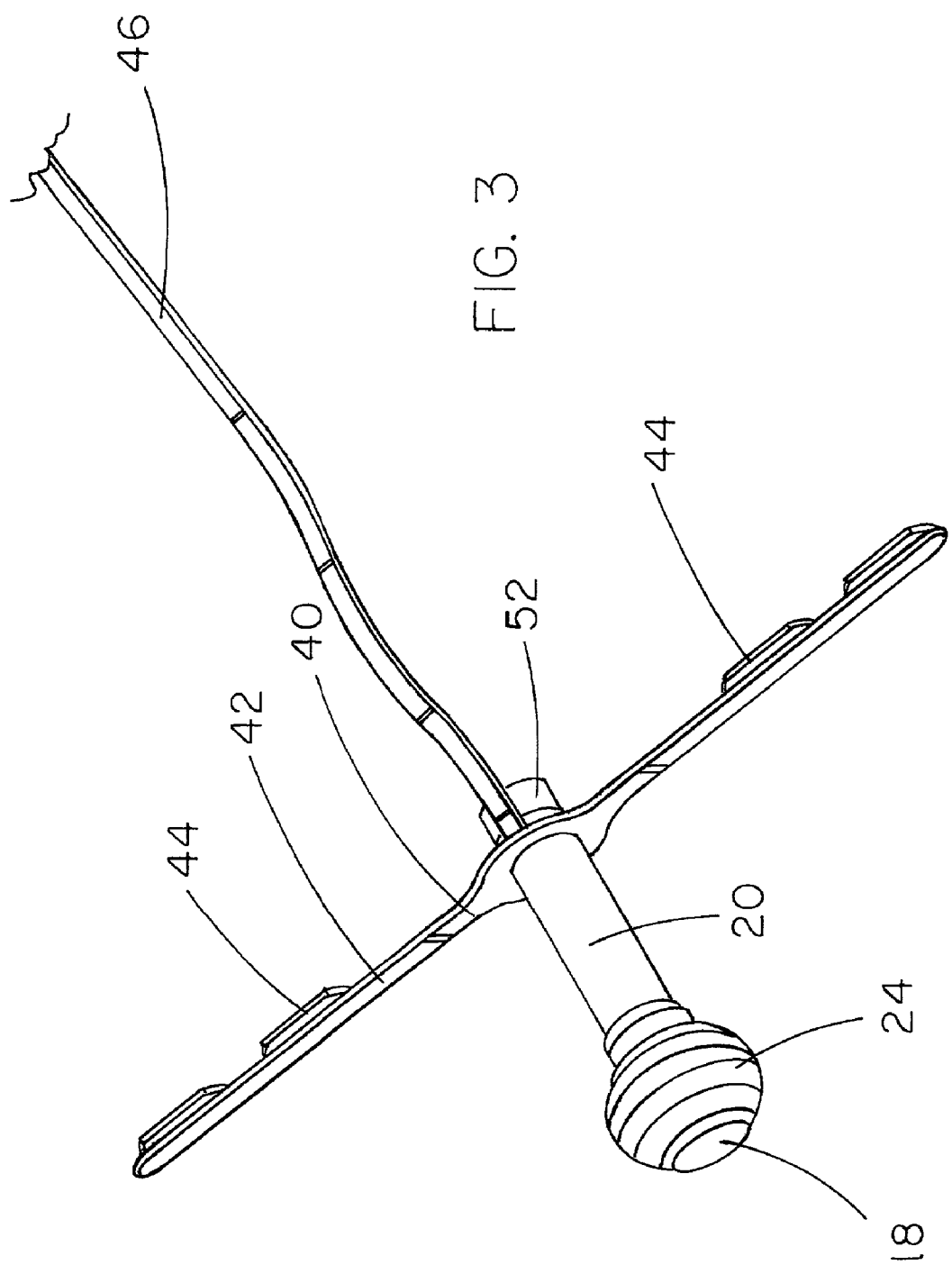

BOWEL MANAGEMENT SYSTEM

FIELD OF THE INVENTION

The present invention relates generally to the field of devices for bowel maintenance, and, more particular, to a rectal catheter having multiple sections of varying durometer hardness and a retention balloon to retain the catheter within the rectum of incontinent patients.

BACKGROUND OF INVENTION

Many circumstances can result in an individual becoming incontinent for an extended period of time. Examples of such circumstances include head or spinal cord trauma, disabling strokes, microbial caused illness, broken lower limbs or pelvic bones, digestive disorders, intensive care stays, and as side effects of administration of various pharmaceuticals. Incontinent patients and their caretakers face a great burden in the maintenance of the bowel and its functions. Such patients often suffer from constipation, but can also experience boughts of diarrhea, which impose even greater nursing problems. Constipation or stool impaction can be painful and require messy bowel irrigations and/or manual disimpaction to break up the impacted stool. Diarrhea, on the other hand, can result in perianal skin breakdown, which in turn can lead to open wounds and infections. The proper treatment of perianal wounds, whether caused by exposure to feces (i.e. diarrhea) or other etiology, can be especially difficult if the wound is continually being contaminated by feces. A great deal of time is necessary to cleanse contaminated wounds, change bedding and treat infections. Thus, there is a great need for devices and methods to improve the function of the bowel in incontinent patients. This need is particularly great in patients who are incontinent as well as being nonambulatory.

Previously, efforts to address these problems included a variety of devices, such as bags or plugs adhered to or inserted into the anus of non-ambulatory patients. These methods are limited in their effectiveness, in part due to leakage around the devices and the resultant effluent that remains in contact with the perianal skin and, in part, due to the complexities of the anal canal anatomy that can interfere with the use of such devices. Because of the ineffectiveness of the available methods for managing fecal evacuation in bed-ridden patients, physicians are frequently forced to construct a stoma in those individuals where enough intact perianal skin does not remain or where the occurrence of an infection would be life threatening.

Thus, it is among the advantages and features of the present invention that it can be used as a bowel maintenance system in a wide variety of incontinent patients for diversion of fecal matter to a receptacle to minimize contact of such fecal matter with patient skin. The new system (1) facilitates the collection of fecal matter for patients requiring stool management (2) provides access for colonic irrigation and (3) provides a conduit through which medications may be administered.

SUMMARY OF INVENTION

Thus, it was with the above disadvantages and limitations in mind that the new bowel management system was developed. The new system is composed generally of a rectal catheter having three distinct portions, each with different elasticity and durometer hardness. A retention balloon mounted on the outer diameter of the patient proximal catheter maintains the catheter in a position within the rectum that provides for atraumatic sealing and anchoring. An optional intralumenal balloon mounted on the inner diameter of the catheter assists in insertion of the device into a patient's rectum and also acts as an anti-reflux valve to obstruct the catheter's evacuation lumen during periods of bowel irrigation or following medication administration for the purpose of retaining the medications in the patient's rectum. An optional faceplate that can be anchored to the patient with tape prevents migration of the retention balloon too far into the rectum. A drainage tube extends outwardly from the external retention faceplate and functions as a conduit to transport waste and irrigation fluids away from the patient to a waste collection bag. A flush/sampling port is located on the drainage tube and provides access for catheter flushing (rinsing) and stool sampling.

The catheter of the new system preferably includes three syringe connectors. One of the connectors is in fluid communication with the retention balloon and one of the connectors is in fluid communication with the intralumenal balloon. These connectors facilitate the inflation/deflation of the respective balloons. The third connector is in fluid communication with an optional irrigation lumen that exits the catheter at the patient proximal tip and is used for bowel irrigation and administration of medication solutions.

Accordingly, in furtherance of the above goals, the present invention is, briefly, a bowel management system for use in a patient. The new system includes a waste collection catheter having at least two distinct sections of varying durometer hardness. A first section, which is patient proximal and which is disposed in the patient's rectum in normal use position, has a first end and a second end, and a durometer hardness in the range of about 50A to about 90A, so that the catheter patient proximal section is stiff enough to automatically maintain an open position for free flow of bowel waste when in normal use position with a retention balloon inflated. However, the first section is soft and pliable enough to permit folding longitudinally for ease of insertion into the rectum of the patient. A second section has a first end connected to the second end of the patient proximal section, and a second end, and a durometer hardness in the range of about 5A to about 49A. The second section can be positioned and retained in the anal canal of the patient for extended periods without distending the sphincters or causing discomfort. The system also includes a selectively collapsible, substantially spherical retention balloon attached coaxially and exterior of the patient proximal first catheter section such that the proximal-most end of the retention balloon is coincident to the proximal-most first end of the patient proximal first section of the waste collection catheter. The substantially spherical retention balloon has an inflated size so as to be sufficiently large enough to retain the patient proximal end of the catheter in the patient's rectum without being so large as to trigger a defecatory response in the patient.

The present invention is also, briefly, the combination of a bowel management system for use in a non-ambulatory patient and a waste collection bag. The bowel management system includes a waste collection catheter having at least two distinct sections of varying durometer hardness including a patient proximal first section, which is disposed in the patient's rectum in normal use position, having a first end and a second end. The durometer hardness of the first section is such that the catheter patient proximal section is stiff enough to automatically maintain an open position for free flow of bowel waste when in normal use position, yet is soft and pliable enough to permit folding longitudinally for ease of insertion into the rectum of a patient. A second section has a first end connected to the second end of the patient proximal first section, and a second end sufficiently spaced from the first end that the second section can be positioned and retained in the anal canal of the patient and has a durometer hardness to permit the retention of the second section in the patient for extended periods without causing discomfort or lesions in the patient. A waste collection bag is adapted for secure, leak-proof connection to the waste collection catheter and is sized sufficiently large enough to receive fecal waste from the patient for extended periods, in the range of at least four hours.

The invention is further, briefly, a method for inserting a bowel management system into a patient, the method including:

(a) providing a bowel management system, the system having:

a waste collection catheter having at least two distinct sections of varying durometer hardness including:

a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with retention balloon inflated, yet is soft and pliable enough to permit folding longitudinally for ease of insertion into the rectum of a patient;

a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient;

(b) folding the patient proximal first end of the waste collection catheter longitudinally;

(c) inserting the folded patient proximal first end of the waste collection catheter into the patient's rectum sufficiently far that the selectively collapsible, substantially spherical retention balloon is entirely within the patient's rectum; and d) securing the waste collection catheter in the position to which it has been inserted so that the catheter does not become separated from the patient during an extended period of time, in the range of hours, while the patient's body waste is permitted to drain out of the patient's body through the waste collection catheter.

The invention is further, briefly, a method for inserting a bowel management system into a patient, the method including:

(a) providing a bowel management system, the system having:

a waste collection catheter having at least two distinct sections of varying durometer hardness including:

a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with retention balloon inflated, yet is soft and pliable enough to permit folding longitudinally for ease of insertion into the rectum of a patient;

a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient;

b) inflating an intralumenal balloon in the patient proximal end of the waste collection catheter to the extent that the intralumenal balloon extends slightly beyond the proximal-most end of the catheter, to thereby provide a curved tip for ease of introduction of the catheter into the patient's rectum (c) inserting the patient proximal first end of the waste collection catheter into the patient's rectum sufficiently far that the selectively collapsible, substantially spherical retention balloon is entirely within the patient's rectum; and (d) securing the waste collection catheter in the position to which it has been inserted so that the catheter does not become separated from the patient during an extended period of time, in the range of hours, while the patient's body waste is permitted to drain out of the patient's body through the waste collection catheter; and (e) deflating the intralumenal balloon in the patient proximal end of the waste collection catheter to permit free flow of body wastes from the patient.

These and other objects and advantages will be in part apparent and in part pointed out herein below.

BRIEF DESCRIPTION OF DRAWINGS

FIG. 3 is a schematic representation of the exterior of the rectal tube subassembly of the system of FIG. 1.

Throughout the drawings like elements are indicated by like element numbers.

DETAILED DESCRIPTION

Figure 1:
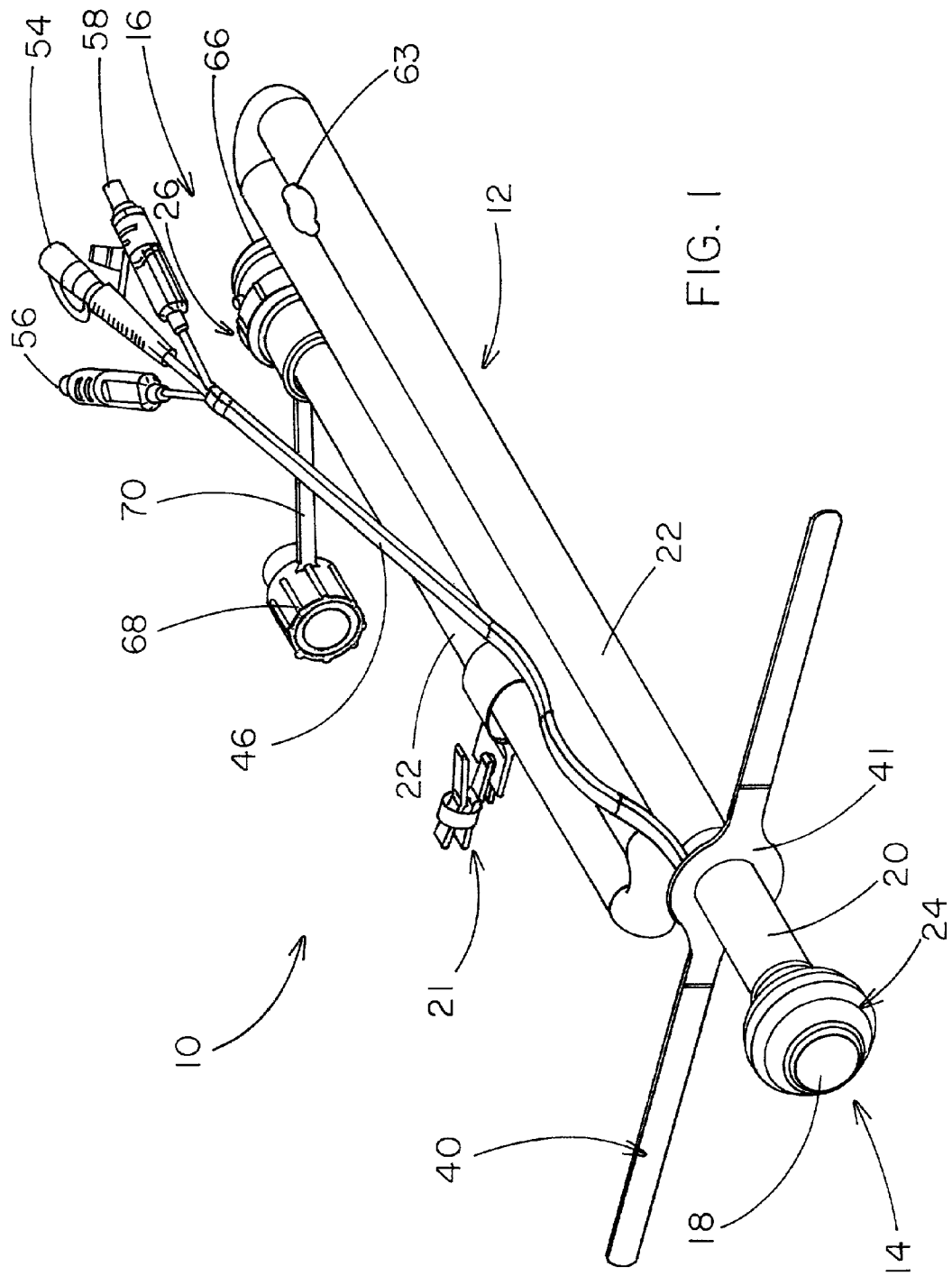
FIG. 1 is a schematic perspective view of a bowel management system constructed in accordance with and embodying the present invention and shown inflated in the use position.
Figure 2:
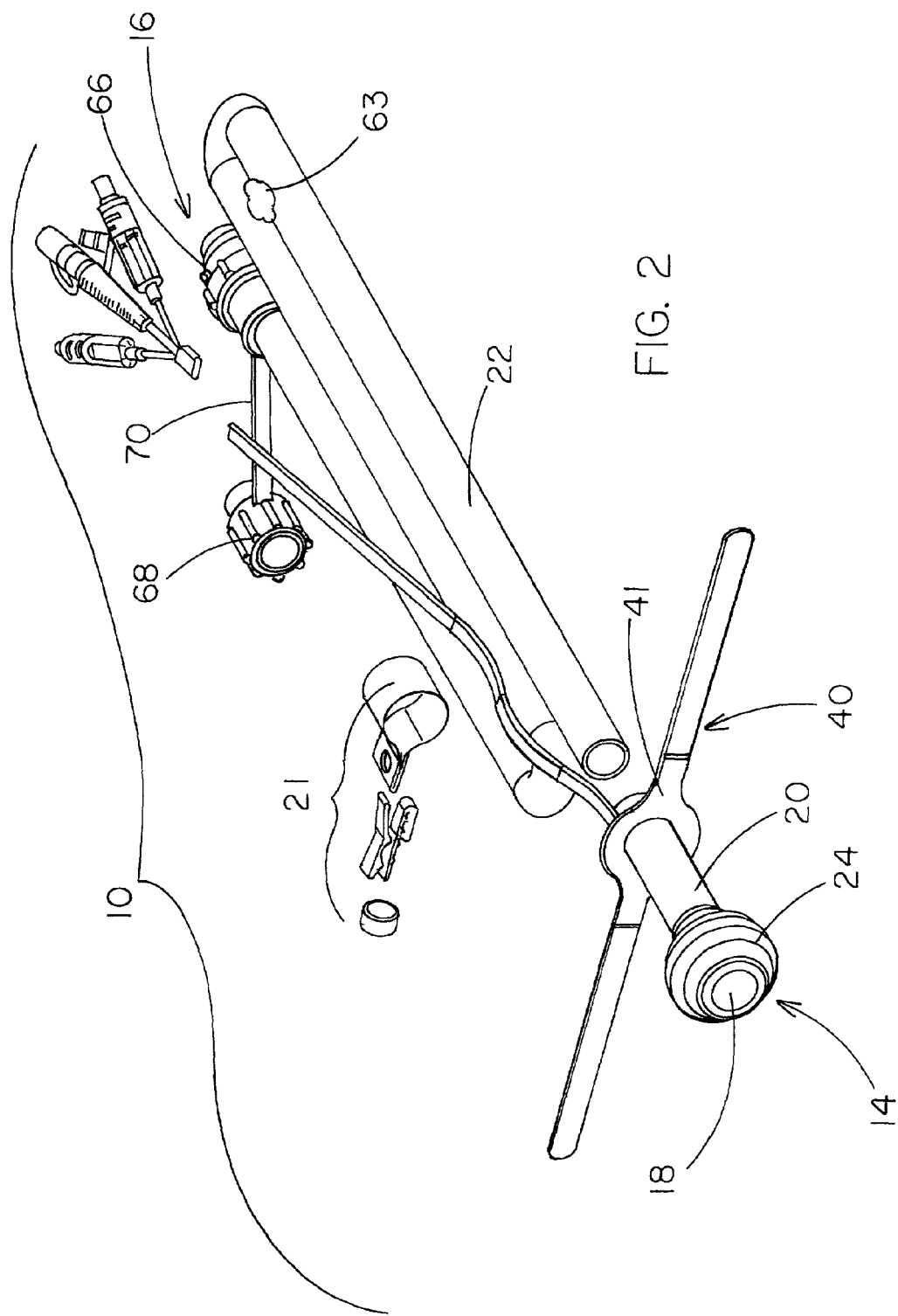
FIG. 2 is a schematic perspective view of the system of FIG. 1, shown partially exploded.

With reference to the figures, and particularly FIGS. 1 and 2, a bowel management system, generally designated 10, includes a catheter 12 having a patient proximal end 14 and a patient distal end 16 and three distinct sections 18, 20, 22 therebetween. Rectal catheter section 18 is located at the proximal end 14 of the catheter, section 20 is a midsection and section 22 is toward the patient distal end 16. A first balloon 24, which is inflatable, is mounted at the patient proximal end 14 of catheter 12 and a bag connector assembly 26 is mounted at the patient distal end 16. These elements will be described in further detail hereafter.

Rectal catheter section 18 has a patient proximal opening that, when positioned for normal use, opens into the rectum of a patient and a second end or distal opening which connects to the second catheter section 20. First catheter section 18 (shown enlarged in FIGS. 8, 9, 10 and 12) is formed of a material having a durometer hard enough to maintain a sufficient opening at the first end of the tube, in order to avoid collapse and subsequent blocking of fecal outflow from the patient. An example of a suitable material is silicone rubber, 80 SH polydimethylsiloxane and fumed silica. The optimal durometer range is between 50A and 90A shore hardness. The proximal opening must be kept open, in order to effectively receive stool entering the first catheter section 18. A relatively large lumen which runs longitudinally within the cylindrical wall of tube section 18 is indicated at number 30 in FIGS. 8, 9, 10 and 12. Smaller lumens 32, 34 are located adjacent and parallel to lumen 30 on opposite sides thereof. Reference numeral 36 denotes an annular shoulder at the proximal end of catheter section 18. The proximal end of bolster ("retention") balloon 24 rests against shoulder 36 when in expanded, inflated use position.

Figure 6:
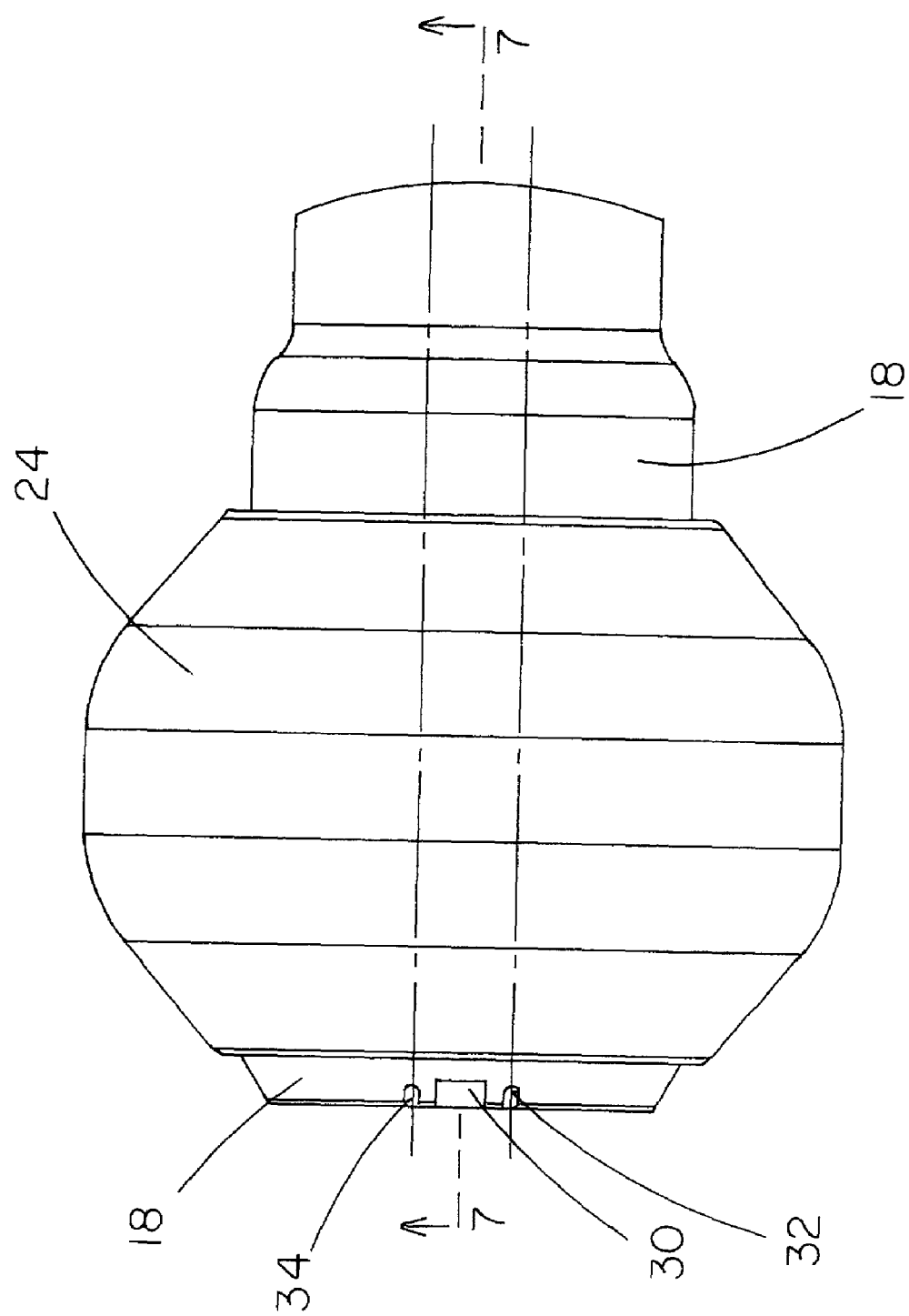
FIG. 6 is a schematic side view of the patient proximal end of the assembled bowel management system.
Figure 7:
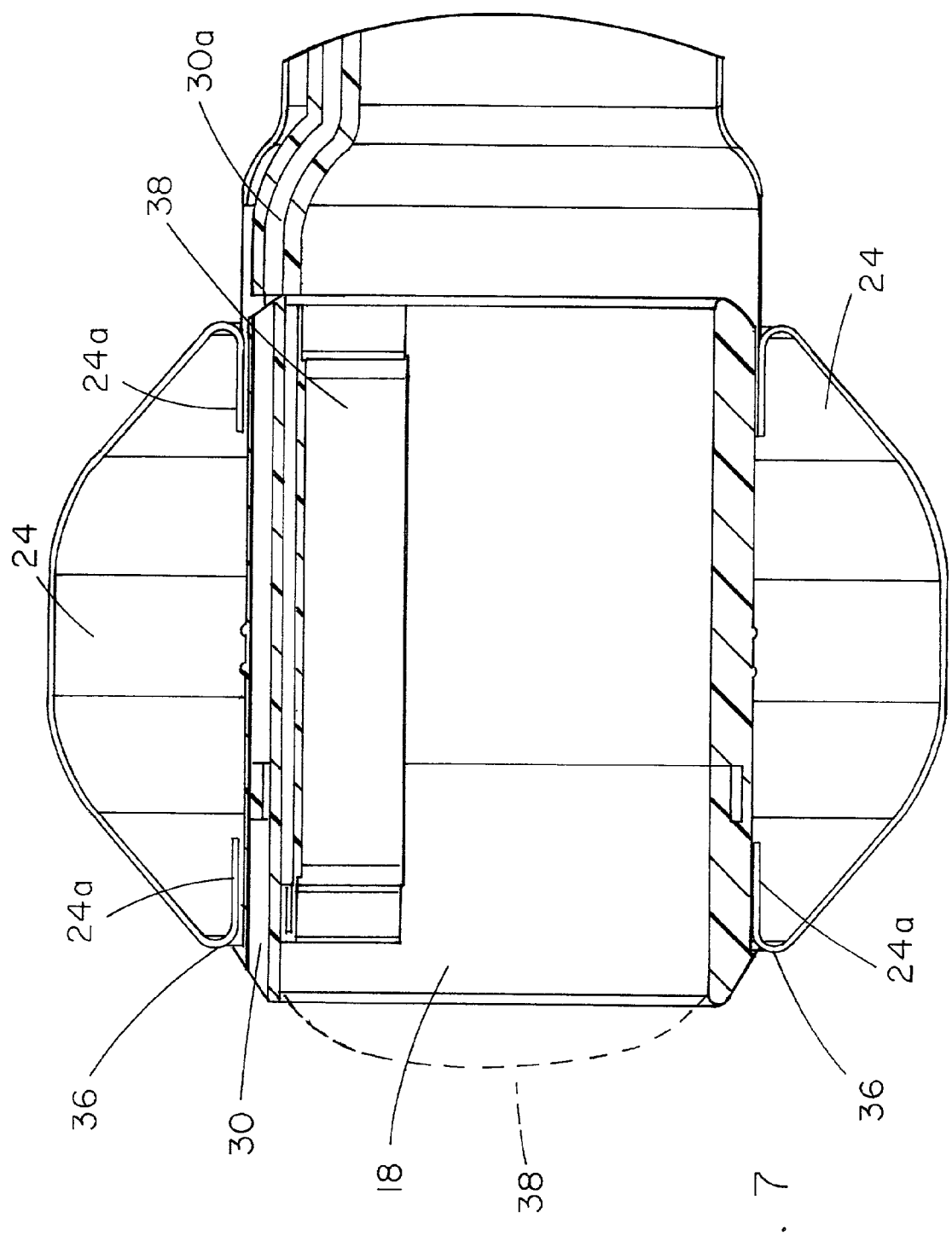
FIG. 7 is a longitudinal section, enlarged, through the patient proximal end of the system of FIG. 1 taken on line 7—7 of FIG. 6 and further enlarged for clarity of detail.
Figure 8:
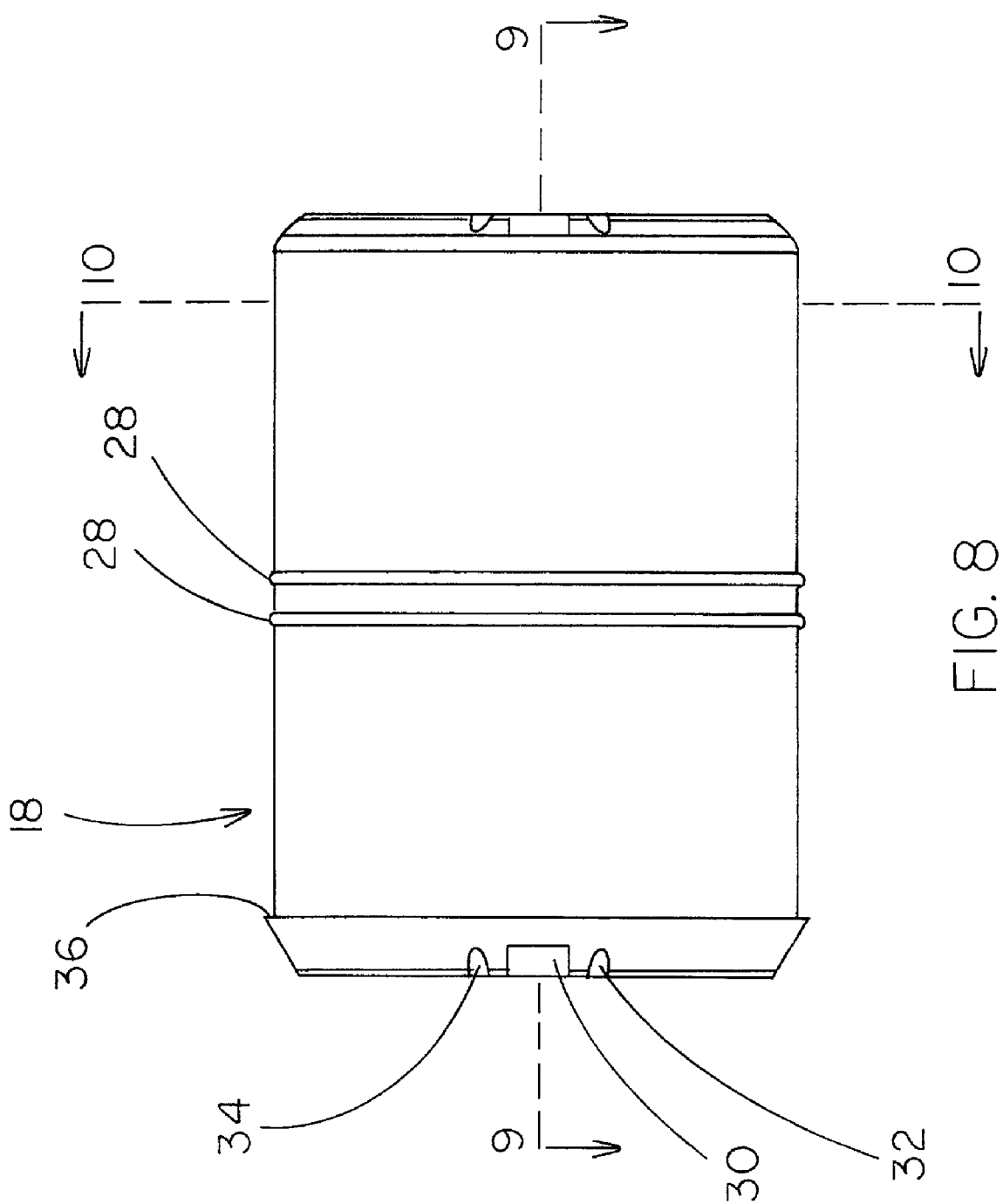
FIG. 8 is an enlarged schematic elevational view of the rectal tube of the assembly of FIG. 1.
Figure 9:
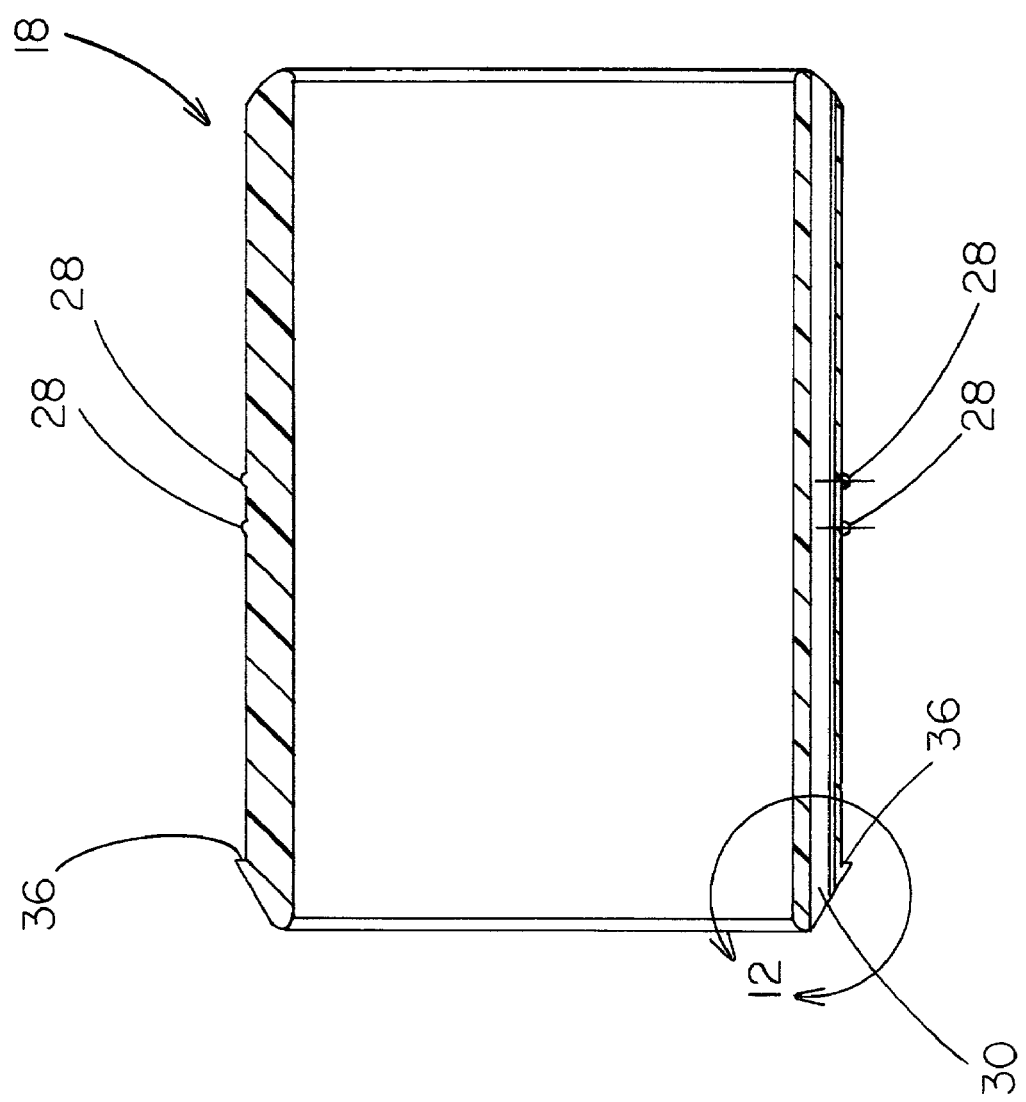
FIG. 9 is a longitudinal sectional view taken on line 9—9 of FIG. 8.
Figure 10:
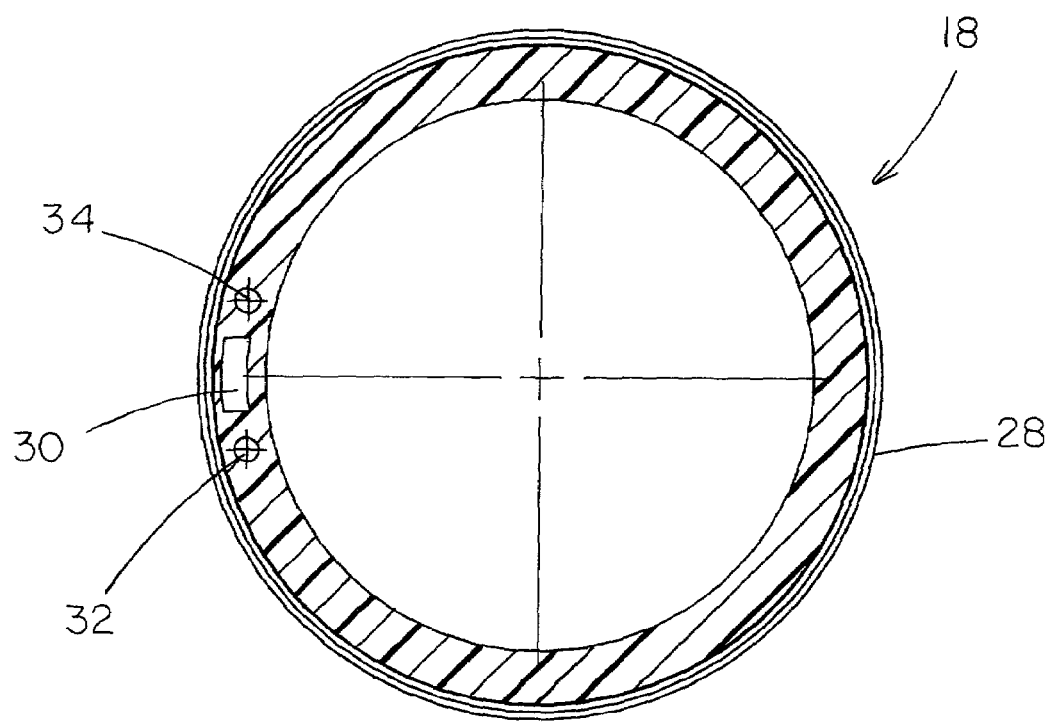
FIG. 10 is a transverse sectional view taken on line 10—10 of FIG. 8.

FIGS. 6 and 7 show enlargements of retention balloon 24 mounted to tube section 18 and show that the proximal end of the balloon 24 is adjacent to and tapers toward the proximal end of tube 18. Retention balloon 24 is formed of a selectively collapsible and inflatable material and is mounted coaxially around the proximal end of section 18 so that the extreme ends of each element are substantially flush (or at least closely adjacent to) with one another.

FIG. 7 is a longitudinal section of FIG. 6, which illustrates internally of tube section 18 an optional intralumenal balloon 38 in a collapsed state. When inflated the intralumenal balloon 38 acts as a anti-reflex valve (ARV) and if inflated sufficiently so that the patient proximal end of balloon 38 protrudes slightly (as shown in phantom in FIG. 7) beyond the proximal end of tube section 18, the intralumenal balloon also acts as an aid to insertion of the bowel management assembly into the patient's rectum. This optional embodiment of the system includes an irrigation lumen 30 (described further herein), which exits the patient proximal end of the catheter section 18 and can be connected to an irrigation supply for inputting irrigant (such as saline) into the patient's rectum.

Figure 3A:
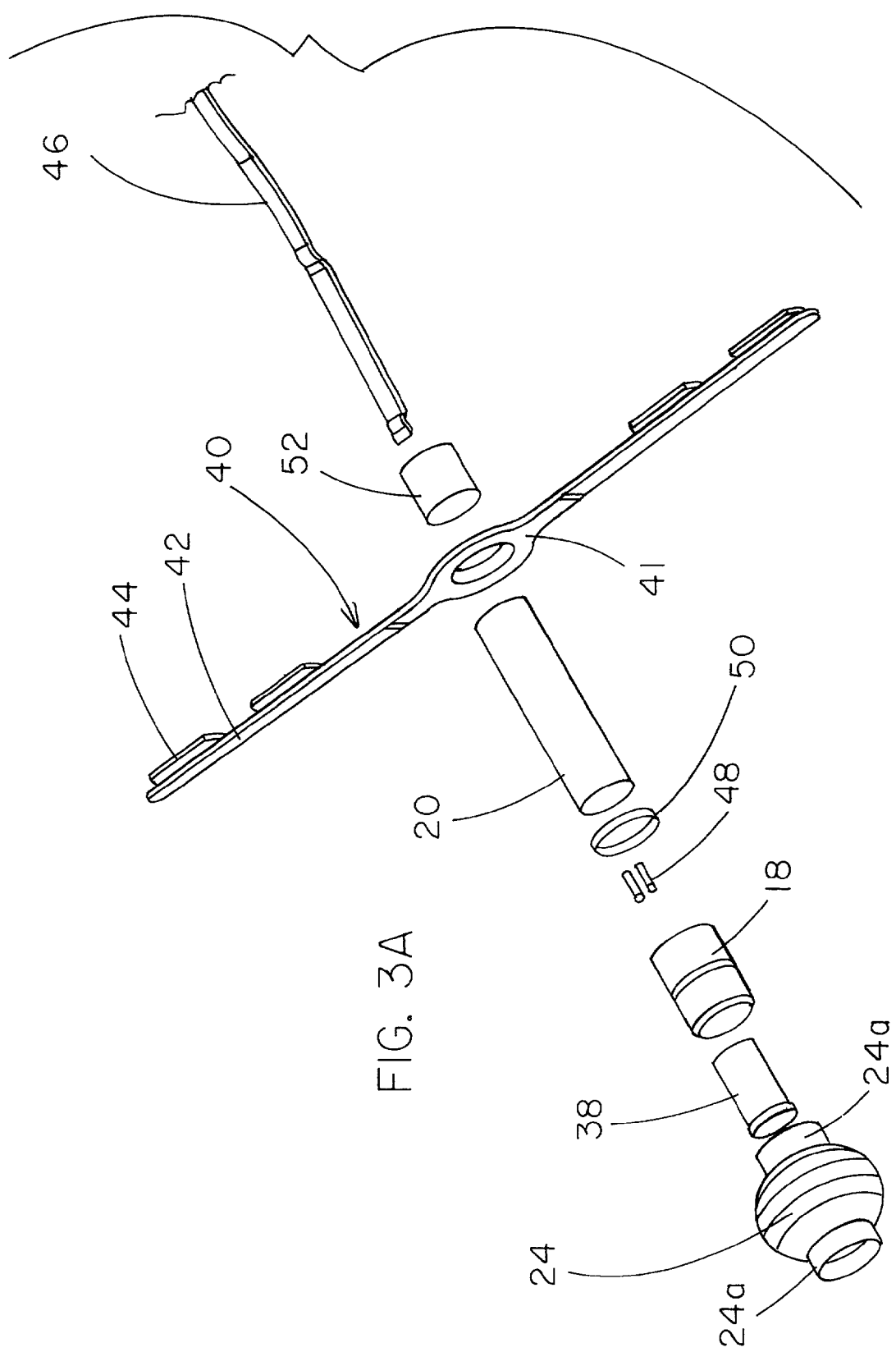
FIG. 3A is an exploded view of the subassembly of FIG. 3.

FIGS. 3 and 3A illustrate assembled and unassembled, respectively, the sub-assembly of the indwelling portion of the new system 10. From the lower left to the upper right of FIG. 3 there is seen the patient proximal catheter section 18 extending just slightly beyond the retention balloon 24 and then the second catheter section 20. Catheter section 20 is a cylindrical tube when completely open. It is formed with a very thin wall from a soft elastic material which results in a collapsible tube that when collapsed, such as by the anal sphincter muscles, creates a very small profile. As this section of the catheter is left in place for very extended periods of time in the patient's anal region this collapsibility is important to prevent loss of the patient's sphincter tone, as could result over time if a large diameter rigid tube where in such place. The optimal durometer range for section 20 is between 5A to 49A shore hardness. A first, proximal, end of the second catheter section 20 is connected to the distal or second end of the first catheter section 18. Catheter section 20 may be constructed as one unitary tube of singular durometer hardness, thickness and diameter. An example of a suitable material for making trans-sphincter catheter section 20 is silicone rubber, 30 SH polydimethylsiloxane and fumed silica.

Figure 11:
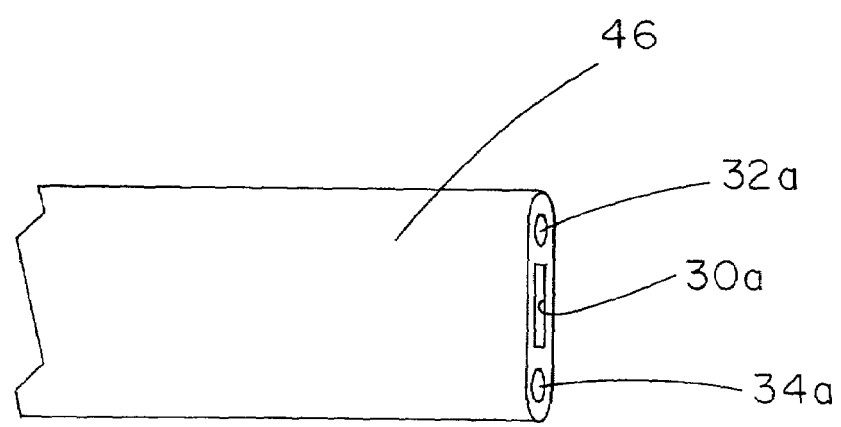
FIG. 11 is an enlarged schematic sectional view of the tri-lumen tube of the assembly of FIG. 1.
Figure 12:
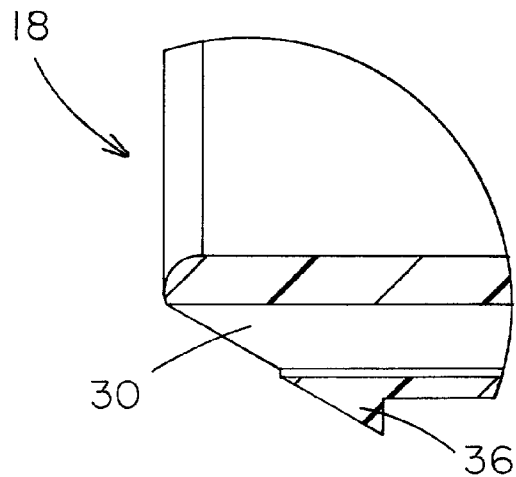
FIG. 12 is an enlarged partial sectional view showing the lumens, taken from FIG. 9.
Figure 13:
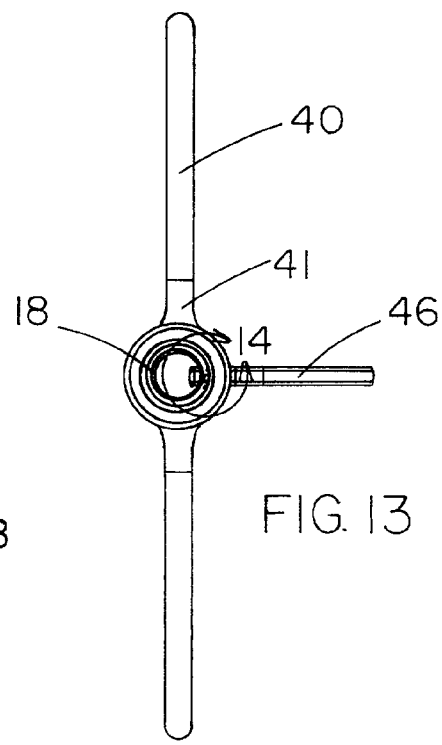
FIG. 13 is a left end elevational view of FIG. 3, rotated.
Figure 14:
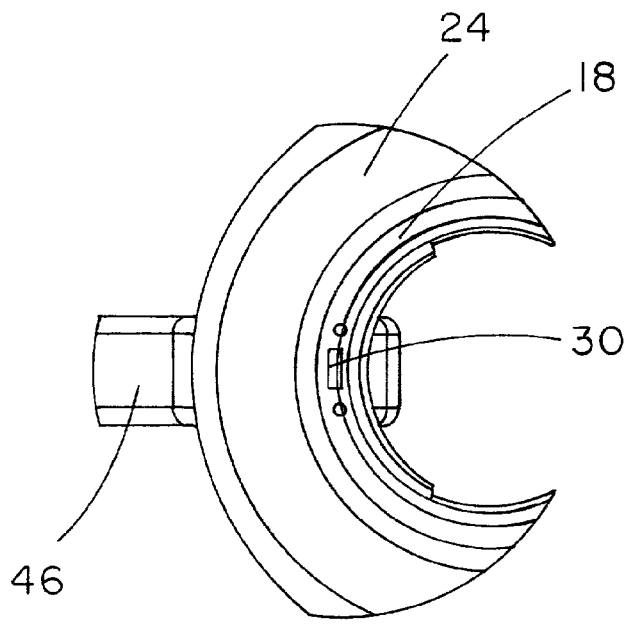
FIG. 14 is an enlarged sectional view taken from FIG. 13 showing the connection of the tri-lumen tube to the rectal tube.

Toward the patient distal end of catheter section 20 there is mounted an optional faceplate 41 which mounts surrounding the tube 20 and has preferably at least two sections 42 extending therefrom. Each extension 42 can have loops or other connectors 44 thereon to facilitate attachment of the faceplate strap 40 to the patient to keep it in place. Finally, in FIG. 3, at the patient distal end of catheter section 20 there is connected an extruded multi-lumen member 46 (shown in enlarged perspective, in FIG. 11) for permitting inflation/deflation of the balloons and flushing of the rectum, if desired. An end view of assembly 10 is provided in FIG. 13, showing the relative positions of the strap 40 and the multi-lumen catheter. An enlarged sectional view (rotated) in FIG. 14 better illustrates the connection of the multi-lumen member 46 with the assembly at catheter section 18. An example of a suitable material for forming multi-lumen member 46 is silicone rubber, 57SH polydimethylsiloxane and fumed silica.

In the exploded view, FIG. 3A, further elements of the subassembly are seen which are hidden or not clear in FIG. 3. This view illustrates retention balloon 24 in its expanded state before application to catheter section 18. The extensions 24A of the symmetrical balloon on each end are annular. In FIG. 7 it is seen more clearly how extensions 24A are folded under and inwardly so as to seal flat against the exterior wall at opposite ends of catheter section 18.

The figures also show the substantially spherical shape of retention balloon 24. This shape is important because it seats naturally in the patient's rectum to prevent leaking around the retention balloon. The shape of the balloon is important to prevent damage to the rectal wall and to achieve optimum sealing to prevent leakage and to effectively funnel fecal matter into the proximal opening of catheter section 18. Thus, the shape needs to be substantially spherical, not elliptical or torrodial.

The size of the balloon when inflated is not only critical to prevent leakage but also to prevent migration of the new system 10 out of the rectum. The optimal size for balloon 24 for the normal adult patient is between 44 cc and 69 cc. It has been shown in the literature that a volume of 90 cc is sufficient to trigger a defecatory response and thus the retention balloon should not be sized to reach this volume. The minimum of 44 cc is critical in order to prevent leakage and outward migration from the rectum of the patient. The size of the balloon as expressed by a length to diameter ratio is 0.75 at the low end of the inflation range, 44 cc, (i.e., the balloon length is 1.35 inches and the balloon diameter would then be 1.8 inches) and 0.61 at the upper end, 69 cc (i.e., a balloon length of 1.35 inches and a balloon diameter of 2.32 inches). It is to be understood that all sizes given herein are for an average adult patient and can be adjusted proportionally for other non-average patients. The retention balloon 24 is inflated via a lumen 34, which opens into the balloon. The lumen is connected via a multi-lumen member 46 to an inflation device, such as a syringe, filled with air or saline or some other biocompatible fluid. The inflation device limits the volume of inflation medium infused to a volume that results in the inflation of the balloon to the desired range of 44 to 69 cc.

An example of a suitable material from which to form retention balloon 24, in order to achieve the desired results is silicone rubber, 30SH polydimethylsiloxane and fumed silica. Alternatively, the retention balloon material itself could limit the size if a material or structure was used that would only expand to the optimum size. An example of such material would be polyimide. An example of such a structure would be a stiff mesh impregnated into an otherwise elastic material such as silicone that would mechanically limit the retention balloon size when inflated. In turning to FIG. 3A, to the right of the retention balloon 24 is shown a second balloon 38 which is illustrated in its collapsed position. Balloon 38 is also illustrated in FIG. 7 collapsed in solid lines and inflated in broken lines. When inflated, balloon 38 fills the lumen of catheter section 18 to block reflux and facilitates insertion of the system into a patient.

Further with reference to FIG. 3A, catheter section 18 is shown then to the right of balloon 38. To the right of catheter section 18 are shown two small TEFLON tubes 48 which interconnect paired small lumen in the multi-lumen catheter 46 to corresponding openings to paired lumen in rectal catheter section 18. An optional radiopaque marker 50 is preferably annular and is useful for accurately determining the location of and position of the assembly portion within the rectum of the patient. Marker 50 is formed for example of material such as a tungsten silicone mixture, which is biocompatible, but easily detected by radiograph. To the right of radiopaque marker 50 in FIG. 3A is shown the trans-sphincter catheter section 20, the midsection of catheter 12. FIGS. 3 and 3A also illustrate the positioning of the faceplate 40 as it is mounted by a through hole onto the patient distal end of mid-catheter section 20. A bridge section or drain tube connector band 52 is illustrated to the right of element 40 in FIG. 3A and also is visible in FIG. 3. Bridge section 52 permits the third, patient distal segment of catheter 12, segment 22 to be connected in abutting relationship with midsection 20, by a slip fit of the sections 20, 22 over (or optionally, under) the segment 52. Extruded multi-lumen member 46 is illustrated at the right of FIG. 3A and is shown in part, enlarged in FIG. 11 for clarity. In this embodiment, the multi-lumen member 46 is relatively flat and elongated and bears a large central lumen 30 flanked by two smaller lumen 32, 34 on opposite sides of lumen 30, as previously discussed.

FIGS. 1 and 2 illustrate three ports (for example, luer-style connectors), which are connectable to the various lumens in multi-lumen member 46. The larger central port 54 attaches to large lumen 30A in the multi-lumen member and is used for connection of a syringe or other infusion device in order to infuse irrigants or medications. An optional port 56 connects to one of the small optional lumens (e.g., 32a) in the multi-lumen member 46 for inflation and deflation of the optional intralumenal balloon 38 with a syringe or other appropriate device. The other small optional port 58 connects to small lumen 34a, in the multi-lumen member 46 in order to inflate and deflate the retention balloon with a syringe or other appropriate device.

Figure 4:
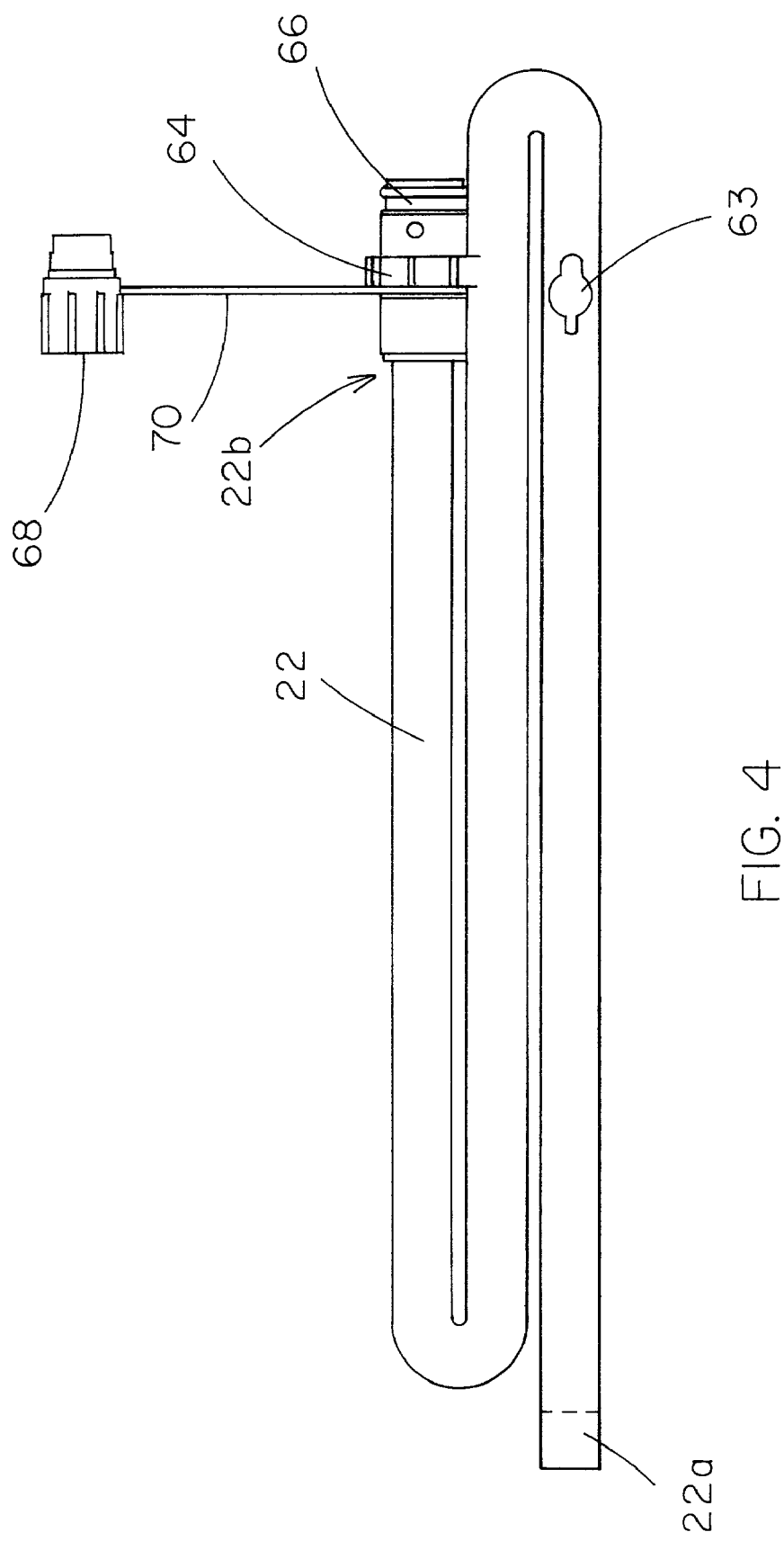
FIG. 4 is a side elevational view of the drainage tube assembly of FIG. 1 with a bag connector attached thereto.
Figure 5:
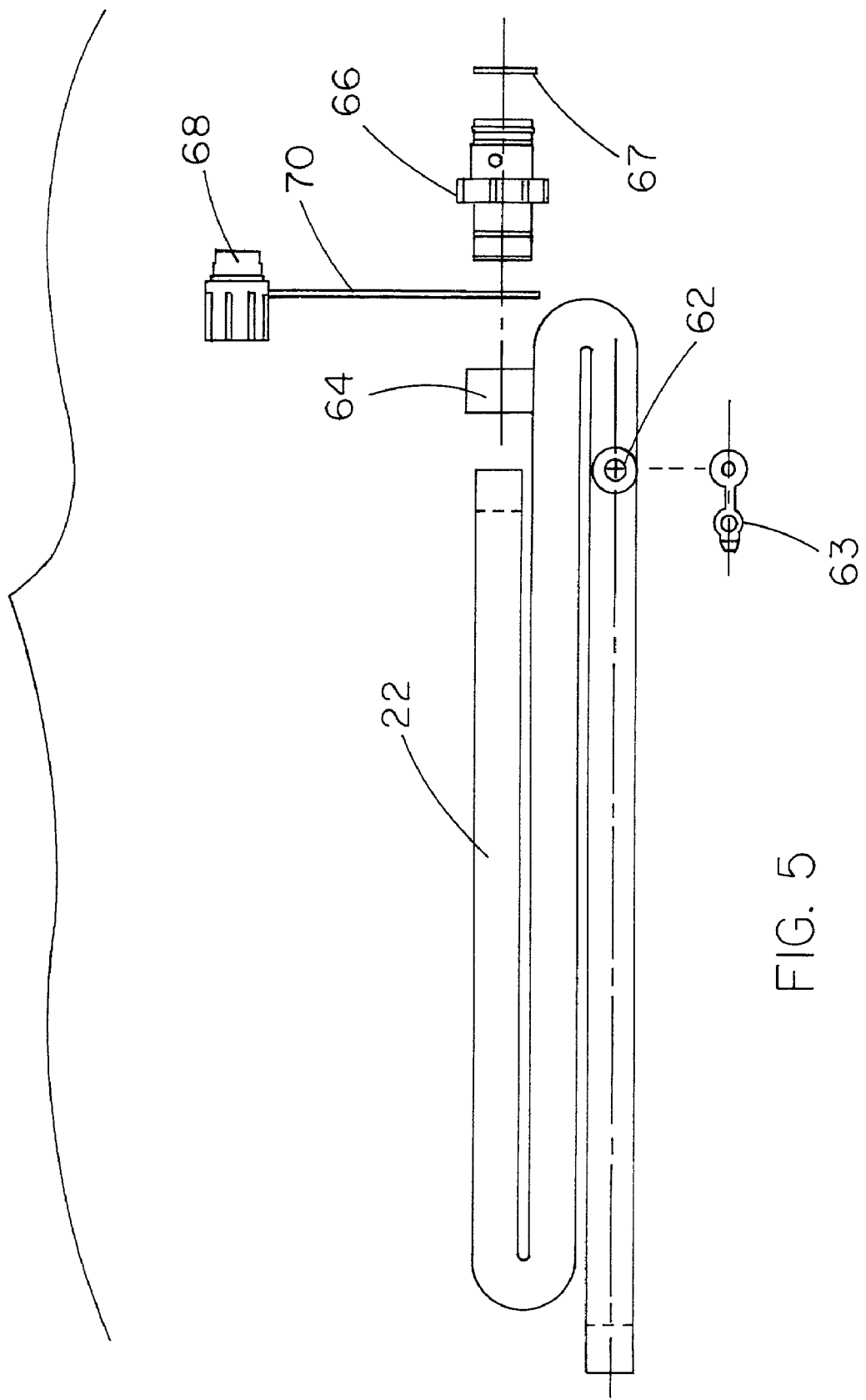
FIG. 5 is an exploded view of FIG. 4.

FIGS. 4 and 5 illustrate the subassembly of the third catheter segment 22. Segment 22 connects at a patient proximal end 22A to the distal end of the trans-sphincter mid-segment 20 and the opposite, patient distal end 22B to a connector 66, which is adapted for connection to a collection bag for example as illustrated at 60 in FIG. 15. The third catheter section 22 is formed of a non-collapsible tube constructed of a material that is stiff enough to maintain its shape to minimize kinking and facilitate drainage of the tube, but soft enough to be "milked" by a care professional to force through fecal material. Optional application of a coating to the exterior of section 2 can facilitate milking thereof and optional internal coating of section 22 facilitates flow-through of feces by decreasing friction against the internal side wall.

Catheter 22 as shown has an optional sampling/flushing port 62 (shown most clearly in FIG. 5) to provide access to the lumen of section 22 for taking fecal samples or for flushing to clean the catheter. In order to prevent bacterial contamination of the catheter and to also aid in reduction of odor to fecal build up in the catheter, frequent flushing through the optional sampling/flushing port 62 is preferred. A cover for port 62, 63 of any suitable variety is also desirable.

The connector assembly 66 illustrated at end 22B of catheter 22 includes a sleeve 64 spacedly along the length of catheter 22 to receive and retain the connector assembly, which attaches 22B to collection bag 60. It may be a heat-shrinkable band or other suitable retention means as desired. As shown in FIG. 5 connector assembly 66 fits into the end 22B and then is adapted, also with an optional O-ring (e.g. 67), to connect in a sealing manner to the bag. A closure portion 68 is also desirable for closing off the connector assembly 64 preventing leakage when the bag is separated from catheter portion 22. If desired, the closure portion 68 may be connected by a string, strip, cord or other piece 70 to end 26.

Figure 15:
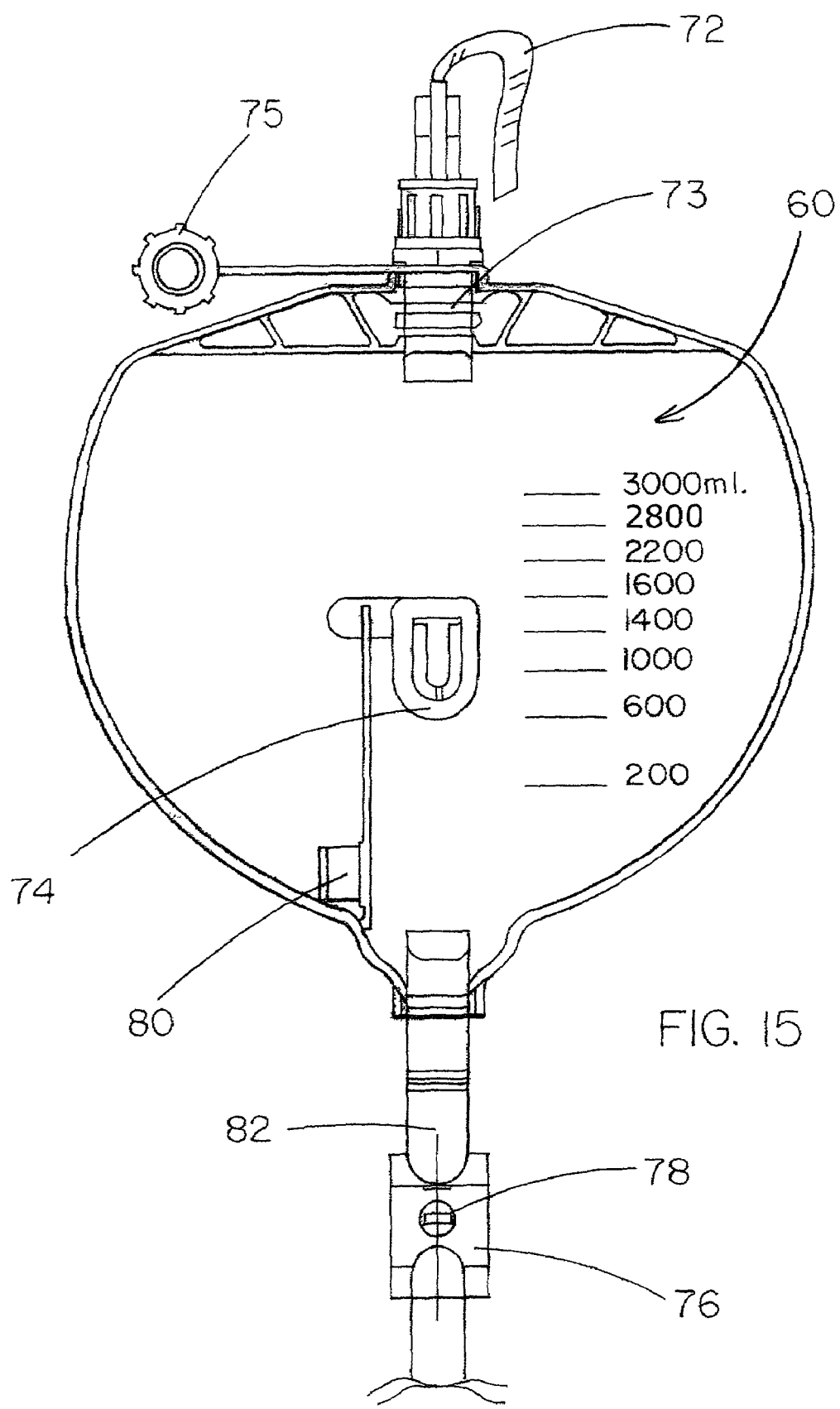
FIG. 15 is a schematic elevational view of a waste collection bag used with the system with its various tubes and connectors.

System 10 catheter section 22 empties into a collection bag 60, which can be hung by the bedside to collect fecal waste matter. FIG. 15 illustrates waste collection bag 60, which is considerably larger than what would ordinarily be used for a colostomy or urinary bag and the bag may be left in place for long periods of time without having to be emptied. It is expected that bag 60 will have approximately a three liter capacity, and be provided with a hook 72 for hanging on the bed or chair and of course a connector 73 for connection to the catheter connector assembly 64 in a sealing manner. The waste bag 60 also optionally carries a drain tube holster 74, such as the U-shaped connector illustrated, for example, and a clamp 76 for sealing off the collection bag drain tube 82. Clamp 76 desirably carries a button 78 or other connector, which slips into holster 74 or otherwise attaches to bag 60. Closure portion 75 is also desirable for preventing leakage from the bag connector 73 when the bag is not connected to the catheter portion 22 of the bowel management system 10. An outlet tube 82 is also provided for draining out the contents of the bag. It is preferred that the bag 60 be suitable for folding up because it is rather long; in order to prevent it from dragging on the floor. Clamp 76 carrying the button holster connector 78 is useful for sealing off collection bag drain tube 82 by pinching it. Also, Cap 80, which is preferably attached to the holster 74 is useful for blocking the open tip (not shown) of bag drain tube 82.

Another optional feature of the new bowel management system is the provision of a faceplate which would serve as a retention mechanism to prevent internal migration of the bowel management system 10, as well as to prevent rotation of the trans-sphincter catheter section 20 of the device. Such a faceplate 41 can be mounted on the bridge section 52 as illustrated, in FIGS. 1 and 2, as one useful example. The faceplate can take the form of a strap, wedge, donut, etc. and would preferably be made of silicone, foam or other soft material to avoid irritation of the patient's skin.

FIGS. 1 and 2 also illustrate a clip assembly 21 for attachment of the assembly 10 to a sheet, bedclothes, etc. It is to be understood that the illustrated embodiment is merely one useful assembly for accomplishing this task. As shown, an elastomeric band surrounds a simple pinch clip for gripping fabric or other thin material for the purpose of holding the assembly in position.

Other useful stabilizing devices are conceived.

Use of the New Bowel Management System:

For insertion of bowel management system 10 into a non-ambulatory patient it is preferred that the patient be in the left side down position, if possible, although other positions may be utilized if necessary due to the patient's clinical condition. The procedure for insertion is performed using recognized aseptic techniques as appropriate.

A device is selected with the appropriate trans-sphincter catheter section length, usually 4 cm for a female patient, or 6 cm for a male patient. And the rectum of the patient is examined to confirm no rectal impaction and to be sure that no lesions or strictures exist which would preclude use of the device. A 60 cc syringe is filled with 35 cc–40 cc water and a 30 cc syringe is filled with 20 cc water. The 30 cc syringe is attached to the intralumenal balloon connector and the intralumenal balloon 38 is filled with the 20 cc's of fluid.

Lubricant is applied to patient proximal end of the device including the protruding intralumenal balloon 38, the deflated retention balloon 24 and the patient's anus. Using the protruding end of the intralumenal balloon as an introducer, the patient proximal end of catheter section 18 is guided through the anus and into the distal rectum.

The 60 cc syringe is attached to the retention balloon connector 58 and the retention balloon 24 is inflated with the syringe contents (in this example, 35 cc–40 cc water). The catheter connector assembly 66 is connected to the waste collection bag connector 73 and bag 60 is positioned at bedside so that the catheter drainage tube 22 is not twisted or kinked. This allows for unobstructed fecal matter flow from the catheter 22 into bag 60.

After the catheter system is inserted into the patient's rectum and connected to the drainage bag, the 30 cc syringe is used to completely aspirate the 20 cc of water (or air) from intralumenal balloon 38. The 30 cc syringe is disconnected from the intralumenal balloon connector.

Catheter/bowel lumenal patency is confirmed by performing the following procedure:

The patient is placed in a slight head up position to promote drainage, the gravity irrigation or enteral feeding bag is filled with one liter of warm tap water and hung from an IV pole two to three feed above the height of patient's anus. The irrigation bag administration set is connected to the catheter irrigation port 54. After the caretaker verifies the connection to the correct catheter port, gravity irrigation is begun. Large stool pieces are broken up by a combination of irrigating and manual douching (i.e. constricting outflow and squeezing the drainage tube repeatedly). Irrigation is discontinued when stool pieces are no longer present in the effluent.

Irrigation of the patient's rectum can be performed using a gravity bag or by using a syringe. In the gravity bag method it is necessary to provide a waste collection bag with at least two liters of available volume. A standard gravity irrigation or enteral feeding bag with pre-attached administration set is used to infuse about a liter of warm tap water into the patient's anus at a flow rate of about one liter in six to ten minutes. The irrigation bag administration set is connected to the catheter system irrigation port and the 30 cc syringe (filled with 20 cc of fluid) is attached to the intralumenal balloon connector and the intralumenal balloon 38 is filled with the 20 cc's of fluid.

With the patient in a slight head down position the flow control valve on the irrigation bag set is opened and fluid is allowed to drain by gravity into the rectum and colon. If leakage occurs past the retention balloon during irrigation more water is injected into the retention balloon up to a maximum inflation volume of 50 cc.

The infused irrigant is permitted to remain as long as prescribed by physician. Then the 20 cc volume of fluid with which the intralumenal balloon was inflated is removed via syringe and the mixed fluid and feces are allowed to drain out of the rectum and colon. If necessary, the patient's position is modified to slight head up. Once irrigation is complete the administration set is disconnected from the catheter irrigation port. Any additional fluid that was injected into the retention balloon is removed by syringe via the retention balloon connector. If necessary the retention balloon may be completely aspirated and refilled to normal use volume (about 35 to about 40 cc).

If irrigation is performed using a syringe instead of a gravity bag preparations are similar, ensuring that sufficient space is available in the waste collection bag, and then a syringe is prepared with about 60 cc of warm tap water. A 30 cc syringe is prepared with about 20 cc of air or water and attached to the intralumenal balloon connector and the intralumenal balloon is inflated. The syringe is connected to the catheter irrigation port. With the patient in a slight head down position the irrigant is slowly injected into the rectum and colon. As with the gravity bag irrigation method, any leakage can be handled by further inflating the retention balloon. Similarly, irrigant is permitted to dwell for a prescribed time and then the fluid is aspirated from the intralumenal balloon with a syringe to allow drainage of fluid and feces out of the rectum and colon. If necessary the patient's position can be modified. Again, if extra fluid was introduced into the retention balloon it can now be released and the waste bag emptied if necessary.

The system irrigation port can be useful for administering medications or enema solutions. In this case, the port is preferably flushed first with about 10 cc to about 20 cc of water before and after administration of enema/medication solution. A syringe is filled with the desired solution to be introduced and a 30 cc syringe is filled with about 20 cc of air or water. After inflating the intralumenal balloon, the solution is injected and the catheter irrigation lumen is flushed as indicated. The syringe is then disconnected from the irrigation port and the solution is permitted to dwell for the prescribed time. The intralumenal balloon is then deflated, preferably by use of a 30 cc syringe, as previously described.

The flush/sampling port of the system can also be used to draw samples of fecal mater by use of a catheter tip syringe attached to the flush/sampling port. This can be very useful for monitoring a patient's progress and for testing purposes.

In view of the foregoing, it will be seen that the several objects of the invention are achieved and other advantages are attained. Although the foregoing includes a description of the best mode contemplated for carrying out the invention various modification s are conceivable.

As various modifications could be made in the constructions herein described and illustrated without departing from the scope of the invention it is intended that all matter contained in the foregoing description or shown in the accompanying drawings shall be interpreted as illustrative rather than limiting.

We claim:

1. A bowel management system for use in a patient comprising: a waste collection catheter having at least two distinct sections of varying durometer hardness including: a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with a retention balloon inflated, yet is soft and pliable enough to permit folding longitudinally for ease of insertion into the rectum of the patient; a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient.

2. The system of claim 1, and further comprising a lumened member which is substantially smaller in diameter than the waste collection catheter and which has a first end and a second end, the first end of the lumened member being connected to the patient proximal first section of the waste collection catheter and being in fluid communication with the selectively collapsible retention balloon, and wherein the second end of the lumened member is connectable to a port for introduction or removal of fluid from the retention balloon, for selective inflation and deflation of the retention balloon as necessary for insertion, retention or removal of the rectal catheter patient proximal segment to or from the patient's rectum.

3. The system of claim 2, wherein the lumened member has at least two independent lumens, each of the lumens being connectable at the second end of the lumened member to a port for introduction or removal of fluid from the system, one of the two lumens being in fluid communication with the first end of the patient proximal segment of the waste collection catheter, to thereby permit introduction of treatment substances to the patient's rectum.

4. The system of claim 1, wherein the retention balloon has an inflated length-to-diameter ratio in the range of about 0.75 to about 0.61, with a volume of about 44 cc to about 69 cc.

5. The system of claim 4, wherein the retention balloon has a length of 1.35 inches and a diameter of 1.8 inches.

6. The system of claim 4, wherein the retention balloon has a length of 1.35 inches and a diameter of 2.32 inches.

7. The system of claim 1, and further comprising an intralumenal balloon mounted to an interior of the patient proximal first segment of the waste collection catheter.

8. The system of claim 7, wherein the intralumenal balloon is in fluid communication with a lumen of the lumened member to thereby permit selective inflation and deflation of the intralumenal balloon and to function as an anti-reflux device.

9. The system of claim 3, and further comprising an intralumenal balloon mounted to the patient proximal end of the waste collection catheter, wherein the lumened member has a first lumen, a second lumen and a third lumen, the first lumen being in fluid communication with the selectively collapsible retention balloon to thereby permit selective inflation and collapse the retention balloon as necessary for insertion, retention or removal of the rectal catheter patient proximal first segment to or from the patient's rectum, the second lumen being in fluid communication with the inside of the patient proximal first segment of the waste collection catheter, to thereby permit introduction of substances to the patient's rectum, and the third lumen being in fluid communication with the intralumenal balloon.

10. The system of claim 1, and further comprising a third section of the waste collection catheter, which is positioned patient distal in normal use.

11. The system of claim 10, wherein the third section of the waste collection catheter is coated internally with a substance to facilitate flow-through of waste matter from the patient.

12. The system of claim 10, wherein the patient distal third section of the waste collection catheter is coated externally with a substance to facilitate "milking" of the waste collection catheter by a caretaker for the patient.

13. The system of claim 10, wherein the patient distal third section of the collection catheter is coated internally with a substance to facilitate flow-through of waste matter from the patient and coated externally with a substance to facilitate "milking" of the waste collection catheter by a caretaker for the patient.

14. A bowel management system for use in a patient comprising: a waste collection catheter having at least two distinct sections of varying durometer hardness including: a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with a retention balloon inflated, yet is soft and pliable enough to permit folding longitudinally for ease of insertion into the rectum of the patient; a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a third section of the waste collection catheter, which is positioned patient distal in normal use, wherein the third section of the catheter has a flush port to thereby permit the infusion of sufficiently large volumes of fluid into the system to permit irrigation of the patient's bowel.

15. The system of claim 10, wherein the patient distal third segment is formed of a non-latex material to ensure against allergic reactions by the patient and the caregiver.

16. The system of claim 10, and further comprising a selectively openable and closeable access port in the patient distal third segment of the waste collection catheter to thereby permit access to the internal catheter for sampling and insertion of medication and fluids.

17. The system of claim 1, and further comprising a connector for permitting facile, releasable attachment of the system to the patient.

18. The system of claim 1, and further comprising at least one flexible strip connected adjacent to the second end of the second section of the waste collection catheter, to thereby provide optional means by which to releasably attach the waste collection catheter to the non-ambulatory patient to stabilize and secure the system in use position.

19. The system of claim 1, and further comprising a face plate of soft, pliable material, the faceplate being disposed adjacent to the second end of the second section of the waste collection catheter to thereby provide stability to the system in use position.

20. The system of claim 10, and further comprising a closure member connectable to the second end of the patient distal third segment of the waste collection catheter.

21. A method for inserting a bowel management system into a patient, the method comprising: (a) providing a bowel management system, the system having: a waste collection catheter having at least two distinct sections of varying durometer hardness including: a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with retention balloon inflated, yet is soft and pliable enough to permit folding longitudinally for ease of insertion into the rectum of a patient; a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient; (b) folding the patient proximal first end of the waste collection catheter longitudinally; (c) inserting the folded patient proximal first end of the waste collection catheter into the patient's rectum sufficiently far that the selectively collapsible, substantially spherical retention balloon is entirely within the patient's rectum; and d) securing the waste collection catheter in the position to which it has been inserted so that the catheter does not become separated from the patient during an extended period of time, in the range of hours, while the patient's body waste is permitted to drain out of the patient's body through the waste collection catheter.

22. A method for inserting a bowel management system into a patient, the method comprising: (a) providing a bowel management system, the system having: a waste collection catheter having at least two distinct sections of varying durometer hardness including: a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with retention balloon inflated, yet is soft and pliable enough to permit folding longitudinally for ease of insertion into the rectum of a patient; a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient; b) inflating an intralumenal balloon in the patient proximal end of the waste collection catheter to the extent that the intralumenal balloon extends slightly beyond the proximal-most end of the catheter, to thereby provide a curved tip for ease of introduction of the catheter into the patient's rectum (c) inserting the patient proximal first end of the waste collection catheter into the patient's rectum sufficiently far that the selectively collapsible, substantially spherical retention balloon is entirely within the patient's rectum; and (d) securing the waste collection catheter in the position to which it has been inserted so that the catheter does not become separated from the patient during an extended period of time, in the range of hours, while the patient's body waste is permitted to drain out of the patient's body through the waste collection catheter; and (e) deflating the intralumenal balloon in the patient proximal end of the waste collection catheter to permit free flow of body wastes from the patient.

23. The method of claim 21, wherein securing the waste collection catheter in the position to which it has been inserted includes the step of inflating the substantially spherical retention balloon so that the ratio of balloon length-to-diameter is in the range of about 0.75 to about 0.61.

24. The method of claim 22, wherein securing the waste collection catheter in the position to which it has been inserted includes the step of inflating the substantially spherical retention balloon so that the ratio of balloon length-to-diameter is in the range of about 0.75 to about 0.61.

25. A method for managing an incontinent patient's bowel, the method comprising: (a) providing a bowel management system, the system having: a waste collection catheter having at least two distinct sections of varying durometer hardness including: a first section which is patient proximal and which is disposed in the patient's rectum in range of about 50A to about 90A, so that the catheter patient proximal section is stiff normal use position, having a first end and a second end, and a durometer hardness in the enough to automatically maintain an open position for free flow of bowel waste when in normal use position with retention balloon inflated, yet is soft and pliable enough to permit folding longitudinally for ease of insertion into the rectum of a patient; a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient; (b) inserting the first section of the waste collection catheter into the patient's rectum; (c) connecting an end opposite the first section of the waste collection catheter to a waste collection vessel; (d) confirming patentcy of the waste collection catheter; (e) permitting body wastes to flow through the waste collection catheter into the waste collection container; (f) emptying the waste collection container from time to time as necessary when the waste collection container becomes filled.

26. The method of claim 25, and further comprising, securing the first section of the waste collection catheter in position by attaching the waste collection catheter to the patient with one or more connection devices.

27. The method of claim 26, wherein the first section of the waste collection catheter is secured in position by attaching the catheter to the patient with strips of tape.

28. The method of claim 25, wherein the first section of the waste collection catheter is secured in position internally of the patient by inflating the inflatable substantially spherical balloon that is attached around the patient proximal first end of the waste collection catheter to the point where the balloon length-to-diameter ratio is in the range of about 0.75 to about 0.61.

29. The method of claim 25, and further comprising irrigating the patient's bowel by providing an intralumenal balloon mounted to the patient proximal end of the waste collection catheter and a lumened member, wherein the lumened member has a first lumen, a second lumen and a third lumen, the first lumen being in fluid communication with the selectively collapsible retention balloon to thereby permit selective inflation and collapse the retention balloon as necessary for insertion, retention or removal of the rectal catheter patient proximal first segment to or from the patient's rectum, the second lumen being in fluid communication with the inside of the patient proximal first segment of the waste collection catheter, to thereby permit introduction of substances to the patient's rectum, and the third lumen being in fluid communication with the intralumenal balloon; providing a further section to the waste collection catheter, the further section having a port therein; infusing sufficiently large volumes of fluid into the system to permit irrigation of the patient's bowel and rinsing of the catheter from time to time, as necessary; inflating the intralumenal balloon to retain the fluid within the patient's bowel, and after a predetermined interval; releasing the irrigation fluid by deflating the intralumenal balloon and permitting the fluid to flow through the waste collection catheter into a waste collection vessel.

30. The method of claim 25, and further permitting the patient's body wastes to flow into a waste collection vessel having a size of at least approximately three liters.

31. The method of claim 25, and further comprising providing the system with a lumened member which is substantially smaller in diameter than the waste collection catheter and which has a first end and a second end, the first end of the lumened member being connected to the patient proximal first section of the waste collection catheter and being in fluid communication with the selectively collapsible retention balloon, and wherein the second end of the lumened member is connectable to a port for introduction or removal of fluid from the retention balloon, for selective inflation and deflation of the retention balloon as necessary for insertion, retention or removal of the rectal catheter patient proximal segment to or from the patient's rectum, wherein the lumened member has at least two independent lumens, each of the lumens being connectable at the second end of the lumened member to a port for introduction or removal of fluid from the system, one of the two lumens being in fluid communication with the first end of the patient proximal segment of the waste collection catheter, to thereby permit introduction of fluid treatment substances to the patient's rectum; and introducing fluid treatment substances to the patient's bowel via the lumened member.

32. The method of claim 31, and further comprising retaining the introduced treatment substances in the patient's bowel for a selected period of time by, providing an intralumenal balloon mounted to the patient proximal end of the waste collection catheter and, after introducing the treatment substances; inflating the intralumenal balloon to block the interior of the catheter; and then, after the selected period of time, deflating the intralumenal balloon to permit passage of fluids from the patient's bowel.

33. A bowel management system for use in a patient comprising: a waste collection catheter having at least two distinct sections of varying durometer hardness including: a first section which is patient proximal and which is disposed in the patient's rectum in normal use position, having a first end and a second end, and a durometer hardness in the range of about 50A to about 90A, so that the catheter patient proximal section is stiff enough to automatically maintain an open position for free flow of bowel waste when in normal use position with a retention balloon inflated, yet is soft and pliable enough to permit folding longitudinally for ease of insertion into the rectum of the patient; a second section having a first end connected to the second end of the patient proximal section, and a second end, and a durometer hardness in the range of about 5A to about 49A, so that the second section can be positioned and retained in the anal canal of the patient for extended periods without distending the sphincters or causing discomfort; and a selectively collapsible, substantially spherical retention balloon attached coaxially and exterior of the patient proximal first catheter section such that the proximal-most end of the retention balloon is coincident to the proximal-most first end of the patient proximal first section of the waste collection catheter, the substantially spherical retention balloon having an inflated size so as to be sufficiently large enough to retain the patient proximal end of the catheter in the patient's rectum without being so large as to trigger a defecatory response in the patient, and further comprising a lumened member which is substantially smaller in diameter than the waste collection catheter and which has a first end and a second end, the first end of the lumened member being connected to the patient proximal first section of the waste collection catheter and being in fluid communication with the selectively collapsible retention balloon, and wherein the second end of the lumened member is connectable to a port for introduction or removal of fluid from the retention balloon, for selective inflation and deflation of the retention balloon as necessary for insertion, retention or removal of the rectal catheter patient proximal segment to or from the patient's rectum.

34. The system of claim 33, wherein the lumened member has at least two independent lumens, each of the lumens being connectable at the second end of the lumened member to a port for introduction or removal of fluid from the system, one of the two lumens being in fluid communication with the first end of the patient proximal segment of the waste collection catheter, to thereby permit introduction of treatment substances to the patient's rectum.

35. The system of claim 33, wherein the retention balloon has an inflated length-to-diameter ratio in the range of about 0.75 to about 0.61, with a volume of about 44 cc to about 69 cc.

36. The system of claim 35, wherein the retention balloon has a length of 1.35 inches and a diameter of 1.8 inches.

37. The system of claim 35, wherein the retention balloon has a length of 1.35 inches and a diameter of 2.32 inches.

38. The system of claim 33, and further comprising an intralumenal balloon mounted to an interior of the patient proximal first segment of the waste collection catheter.

39. The system of claim 38, wherein the intralumenal balloon is in fluid communication with a lumen of the lumened member to thereby permit selective inflation and deflation of the intralumenal balloon and to function as an anti-reflux device.

40. The system of claim 34, and further comprising an intralumenal balloon mounted to the patient proximal end of the waste collection catheter, wherein the lumened member has a first lumen, a second lumen and a third lumen, the first lumen being in fluid communication with the selectively collapsible retention balloon to thereby permit selective inflation and collapse the retention balloon as necessary for insertion, retention or removal of the rectal catheter patient proximal first segment to or from the patient's rectum, the second lumen being in fluid communication with the inside of the patient proximal first segment of the waste collection catheter, to thereby permit introduction of substances to the patient's rectum, and the third lumen being in fluid communication with the intralumenal balloon.

41. The system of claim 33, and further comprising a third section of the waste collection catheter, which is positioned patient distal in normal use.

42. The system of claim 41, wherein the third section of the waste collection catheter is coated internally with a substance to facilitate flow-through of waste matter from the patient.

43. The system of claim 41, wherein the patient distal third section of the waste collection catheter is coated externally with a substance to facilitate "milking" of the waste collection catheter by a caretaker for the patient.

44. The system of claim 41, wherein the patient distal third section of the collection catheter is coated internally with a substance to facilitate flow-through of waste matter from the patient and coated externally with a substance to facilitate "milking" of the waste collection catheter by a caretaker for the patient.

* * * * *